(12) United States Patent
Bharat et al.

(10) Patent No.: US 11,259,774 B2
(45) Date of Patent: Mar. 1, 2022

(54) REGISTRATION OF OPTICAL SHAPE SENSING TOOL

(71) Applicant: KONINKLIJKE PHILIPS N.V., Eindhoven (NL)

(72) Inventors: Shyam Bharat, Arlington, MA (US); Ehsan Dehghan Marvast, New York, NY (US); Molly Lara Flexman, Melrose, MA (US); Jochen Kruecker, Washington, DC (US); Marissa Patricia Dreyer, Ketchum, ID (US); Amir Mohammad Tahmasebi Maraghoosh, Melrose, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 934 days.

(21) Appl. No.: 15/531,778

(22) PCT Filed: Nov. 30, 2015

(86) PCT No.: PCT/IB2015/059205
§ 371 (c)(1),
(2) Date: May 31, 2017

(87) PCT Pub. No.: WO2016/088013
PCT Pub. Date: Jun. 9, 2016

(65) Prior Publication Data
US 2017/0265840 A1     Sep. 21, 2017

Related U.S. Application Data

(60) Provisional application No. 62/085,668, filed on Dec. 1, 2014.

(51) Int. Cl.
*A61B 8/08* (2006.01)
*A61B 34/20* (2016.01)
(Continued)

(52) U.S. Cl.
CPC ............ *A61B 8/0841* (2013.01); *A61B 5/061* (2013.01); *A61B 17/3403* (2013.01);
(Continued)

(58) Field of Classification Search
CPC ........ A61B 8/0841; A61B 5/061; A61B 34/20
See application file for complete search history.

(56) References Cited

U.S. PATENT DOCUMENTS

| 8,948,081 B2 | 2/2015 | Sudak et al. |
| 2003/0065260 A1* | 4/2003 | Cheng ................. A61B 8/0833 600/427 |

(Continued)

FOREIGN PATENT DOCUMENTS

WO     2011/059888     5/2011

*Primary Examiner* — Hien N Nguyen

(57) ABSTRACT

An intervention system employs an optical shape sensing tool (32) (e.g., a brachytherapy needle having embedded optical fiber(s)) and a grid (50, 90) for guiding an insertion of the optical shape sensing tool (32) into an anatomical region relative to a grid coordinate system. The intervention system further employs a registration controller (74) for reconstructing a segment or an entirety of a shape of the optical shape sensing tool (32) relative to a needle coordinate system, and for registering the needle coordinate system to the grid coordinate system as a function of a reconstructed segment/entire shape of the optical shape sensing tool (32) relative to the grid (50, 90) (i.e., reconstruction of a segment/entire shape of the OSS needle inserted into/through the grid serving as a basis for the grid/needle coordinate system registration).

12 Claims, 7 Drawing Sheets

(51) Int. Cl.
  *A61B 5/06* (2006.01)
  *A61N 5/10* (2006.01)
  *A61B 17/34* (2006.01)
  *A61B 8/00* (2006.01)

(52) U.S. Cl.
  CPC ............ A61B 34/20 (2016.02); A61N 5/1007 (2013.01); *A61B 8/58* (2013.01); *A61B 2017/3411* (2013.01); *A61B 2017/3413* (2013.01); *A61B 2034/2061* (2016.02)

(56) References Cited

U.S. PATENT DOCUMENTS

| | | | |
|---|---|---|---|
| 2003/0158562 A1* | 8/2003 | Feigl | A61B 17/0482 606/148 |
| 2004/0131299 A1* | 7/2004 | Adoram | A61B 8/0833 385/12 |
| 2009/0030339 A1 | 1/2009 | Cheng et al. | |
| 2009/0093715 A1* | 4/2009 | Downey | A61B 8/0833 600/437 |
| 2013/0188855 A1* | 7/2013 | Desjardins | A61B 90/98 382/131 |
| 2014/0088555 A1* | 3/2014 | Li | A61M 5/158 604/506 |
| 2014/0121501 A1* | 5/2014 | Fichtinger | A61B 8/587 600/424 |
| 2014/0206988 A1 | 7/2014 | Ramachandran et al. | |
| 2016/0030130 A1 | 2/2016 | Tahmasebi Maraghoosh et al. | |

* cited by examiner

US 11,259,774 B2

REGISTRATION OF OPTICAL SHAPE SENSING TOOL

CROSS-REFERENCE TO PRIOR APPLICATIONS

This application is the U.S. National Phase application under 35 U.S.C. § 371 of International Application Serial No. PCT/IB2015/059205, filed on Nov. 30, 2015, which claims the benefit of U.S. Application Ser. No. 62/085,668, filed on Dec. 1, 2014. These applications are hereby incorporated by reference herein.

FIELD OF THE INVENTION

The present invention generally relates to an ultrasound-guided intervention involving a registration of a needle to a three-dimensional ("3D") ultrasound volume (e.g., a biopsy procedure and a brachytherapy procedure). The present invention specifically relates to registering an optical shape sensing tool to the 3D ultrasound volume.

BACKGROUND OF THE INVENTION

Generally, a stepper is utilized to hold/guide and if needed, translate/rotate interventional tool(s) for facilitating an ultrasound-guided intervention (e.g., transperineal biopsy, internal radiation therapies such as permanent radioactive seed implants, temporary interstitial brachytherapy, etc.)

More particularly, brachytherapy procedures involve the use of a stepper to hold and translate/rotate a transrectal ultrasound ("TRUS") probe within a patient. The stepper is also used to hold a grid in a fixed position with respect to the TRUS probe for guiding an insertion of needles into the patient.

For example, FIG. 1A illustrates a typical brachytherapy set-up involving a stepper having a frame 40 supporting a grid 50 and a carriage 41 holding a TRUS probe 20. During the brachytherapy procedure, grid 50 is strategically positioned relative to a rectum of the patient, and a gear assembly (not shown) of the stepper is manually or automatically operated to translate and/or rotate TRUS probe 20 in and out of the patient's rectum. Once TRUS probe 20 is properly positioned within the patient's rectum, grid 50 may be used to guide an insertion of one or more needle(s) 30 into the target anatomy (e.g., prostate gland) to facilitate an implantation of radiation source(s) within the patient.

During the brachytherapy procedure, each channel 51 of grid 50 is pre-operatively registered to the 3D ultrasound volume generated by TRUS probe 20 as well known in the art. For example, as shown in FIG. 1A, a grid coordinate system 52 of grid 50 having an origin established at a lower left corner of grid 50 is pre-operatively registered to an image coordinate system 21 of TRUS probe 20 having an origin established by a transducer array (not shown) of TRUS probe 20.

Also during the brachytherapy procedure, it is necessary to register needle 30 to grid 50 for purposes of tracking needle 30 within the 3D ultrasound volume, particularly a tip of needle 30.

Specifically, a hub 60 is attached to a proximal end of needle 30 for establishing a needle coordinate system 31 having an origin at the proximal attachment point of hub 60 to needle 30. An estimation of six (6) registration parameters is required to facilitate a registration of needle coordinate system 31 to grid coordinate system 52. The six (6) registration parameters include:

(1) a width translational parameter $X_{TP}$ indicative of a registration distance between the X axes of coordinate systems 31 and 52 as best shown in FIG. 1B with needle 30 being inserted within a middle channel of grid 50;

(2) a height translational parameter $Y_{TP}$ indicative of a registration distance between the Y axes of coordinate systems 31 and 52 as best shown in FIG. 1B with needle 30 being inserted within the middle channel of grid 50;

(3) a depth translational parameter $Z_{TP}$ indicative of a registration distance between the Z axes of coordinate systems 31 and 52 as best shown in FIG. 1A;

(4) a pitch rotational parameter $X_{RP}$ (not shown) indicative of an angular rotation of needle 30 relative to X axis of needle coordinate system 31;

(5) a yaw rotational parameter $X_{RP}$ (not shown) indicative of an angular rotation of needle 30 relative to Y axis of needle coordinate system 31; and (6) a roll rotational parameter $Z_{RP}$ indicative of an angular rotation of needle 30 about the Z axis of needle coordinate system 31 as best shown in FIG. 1B.

Referring to FIG. 1B, as known in the art, non-zero values of width translational parameter $X_{TP}$ and height translational parameter $Y_{TP}$ may be estimated from a position of channel 51 selected to guide needle 30 relative to grid coordinate system 52. Also, assuming hub 60 is relaxed, needle 30 will enter and exit the selected channel 51 perpendicular to a surface of grid 50 whereby zero values may be estimated for the pitch rotational parameter $X_{RP}$ and the yaw rotational parameter $Y_{RP}$. However, estimations for depth translational parameter $Z_{TP}$ and roll rotational parameter $Z_{RP}$ are not similarly achievable based on the selected channel 51.

As known in the art, with coordinate systems 21 and 52 being registered, registering needle coordinate system 31 to grid coordinate system 52 is equivalent to registering needle coordinate system 31 to image coordinate system 21. Thus, to facilitate a registration of needle coordinate system 31 to coordinate systems 21 and 52, ultrasound sensing and electromagnetic tracking technologies have been proposed to provide for the estimations for depth translational parameter $Z_{TP}$ and roll rotational parameter $Z_{RP}$. While such technologies have proven to be beneficial for tracking the tip of needle 30 in the 3D ultrasound volume, the present invention provides alternative methods for estimating depth translational parameter $Z_{TP}$ and roll rotational parameter $Z_{RP}$ to thereby track a shape of a segment or an entirety of needle 30 as needed for the procedure.

SUMMARY OF THE INVENTION

The alternative methods of the present invention are premised on an incorporation of optical shape sensing ("OSS") tools into the ultrasound-guided interventions (e.g., OSS needle, catheter and guidewires), which facilitates a real-time reconstruction of a shape of a segment or an entirety of the OSS tool relative to the grid (e.g., the OSS tool being inserted into/through a channel of the grid) as a basis for estimating a segment or an entire tool track as well as the depth translational parameter $Z_{RP}$ and roll rotational parameter $Z_{RP}$ to thereby register the image, grid and needle coordinate systems.

For purposes of the present invention, the term "optical shape sensing ("OSS") tool" broadly encompasses any tubular body structural design for interventional procedures as known in the art prior to and subsequent to the present invention (e.g., needles, catheters, and guidewires) whereby optical sensors are embedded within/affixed onto the tubular body. Examples of such optical sensors include, but are not limited, fiber Bragg gratings of optical fibers embedded within/affixed onto a brachytherapy/biopsy needle, a catheter, or a guidewire.

One form of the present invention is an intervention system employing an OSS tool (e.g., a brachytherapy needle having embedded optical fibers) and a grid for guiding an insertion of the OSS tool into an anatomical region (e.g., cranial, thoracic, mammary, abdominal, genital, pubic, etc.) relative to a grid coordinate system (e.g., manual or robotic guidance). The intervention system further employs a registration controller for reconstructing a shape of a segment or an entirety of the OSS tool relative to a needle coordinate system, and for registering the needle coordinate system to the grid coordinate system based on a reconstructed shape of the segment or the entirety of the OSS tool relative to the grid (i.e., reconstruction of a segment/entire shape of the OSS tool inserted into/through the grid serving as a basis for the grid/needle coordinate system registration).

For purposes of the present invention, the term "registration controller" broadly encompasses all structural configurations of an application specific main board or an application specific integrated circuit housed within or linked to a computer or another instruction execution device/system for controlling an application of various inventive principles of the present invention as subsequently described herein. The structural configuration of the registration controller may include, but is not limited to, processor(s), computer-usable/computer readable storage medium(s), an operating system, peripheral device controller(s), slot(s) and port(s). Examples of a computer includes, but is not limited to, a server computer, a client computer, a workstation and a tablet.

A second form of the present invention is the reconstruction controller including a shape reconstruction module for reconstructing a shape of a segment or an entirety of the OSS tool relative to a needle coordinate system, and a tool registration module for registering the needle coordinate system to the grid coordinate system based on a reconstructed shape of the segment or the entirety of the OSS tool relative to the grid (i.e., reconstruction of a segment/entire shape of the OSS tool inserted into/through the grid serving as a basis for the grid/needle coordinate system registration).

For purposes of the present invention, the term "module" broadly encompasses an application component of the registration controller consisting of an electronic circuit or an executable program (e.g., executable software and/firmware).

A third form of the present invention is an interventional method involving an insertion of an OSS tool into a grid relative to a grid coordinate system (e.g., manual or robotic insertion), the reconstruction controller reconstructing a shape of a segment or an entirety of the OSS tool relative to a needle coordinate system, and the reconstruction controller registering the needle coordinate system to the grid coordinate system based on the reconstructed shape of the segment or the entirety of the OSS needle relative to the grid.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

Figure 1:
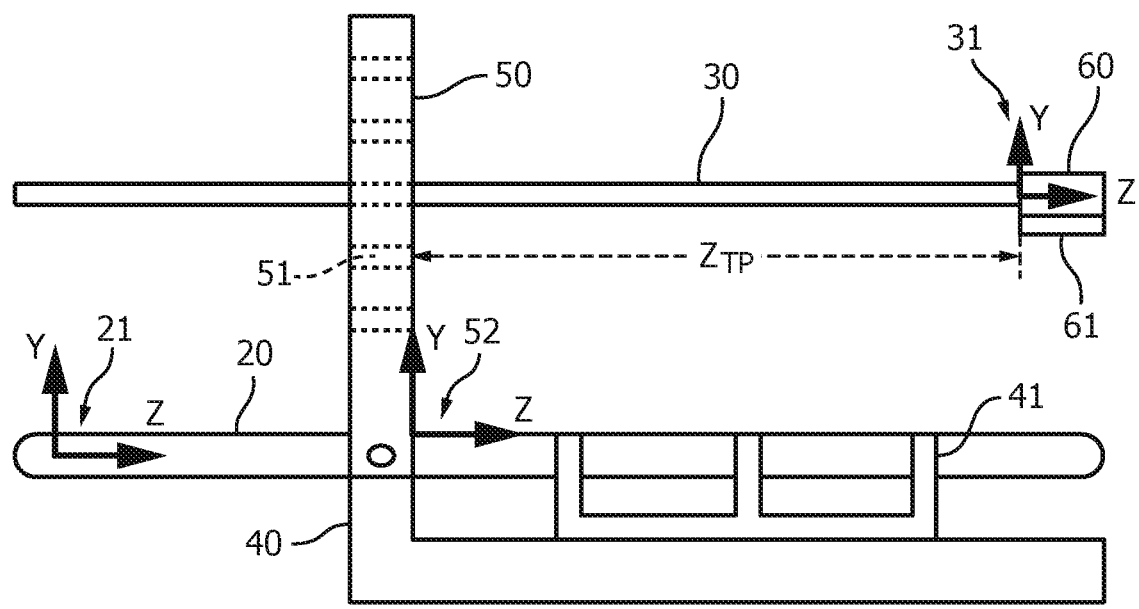
FIGS. 1A and 1B illustrate an exemplary brachytherapy set-up of an ultrasound probe, a brachytherapy needle, a steeper and a grid as known in the art.
Figure 1B:
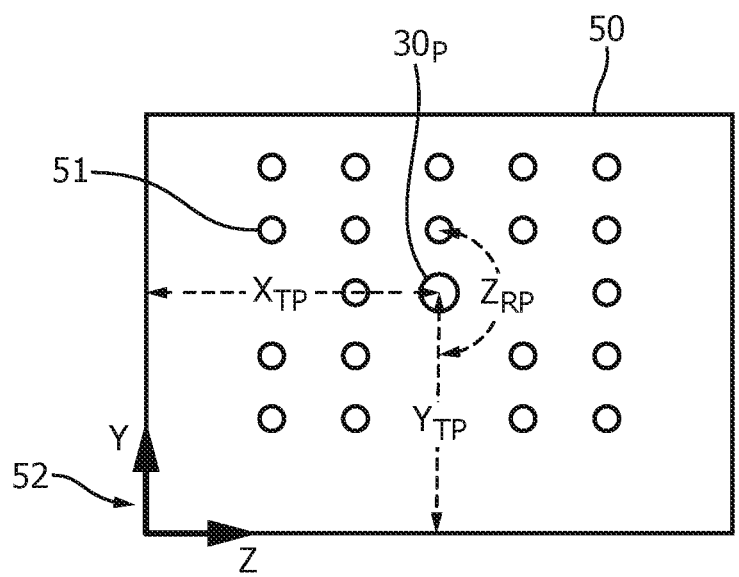
Figure 2:
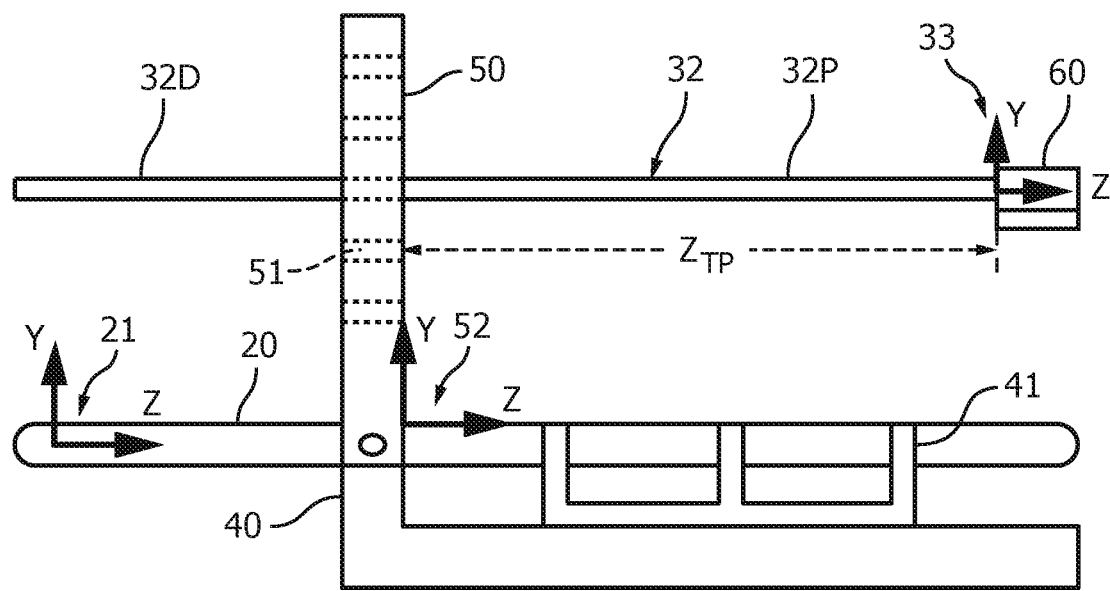
FIG. 2 illustrates an exemplary embodiment of an intervention system in accordance with the present invention.
Figure 2:
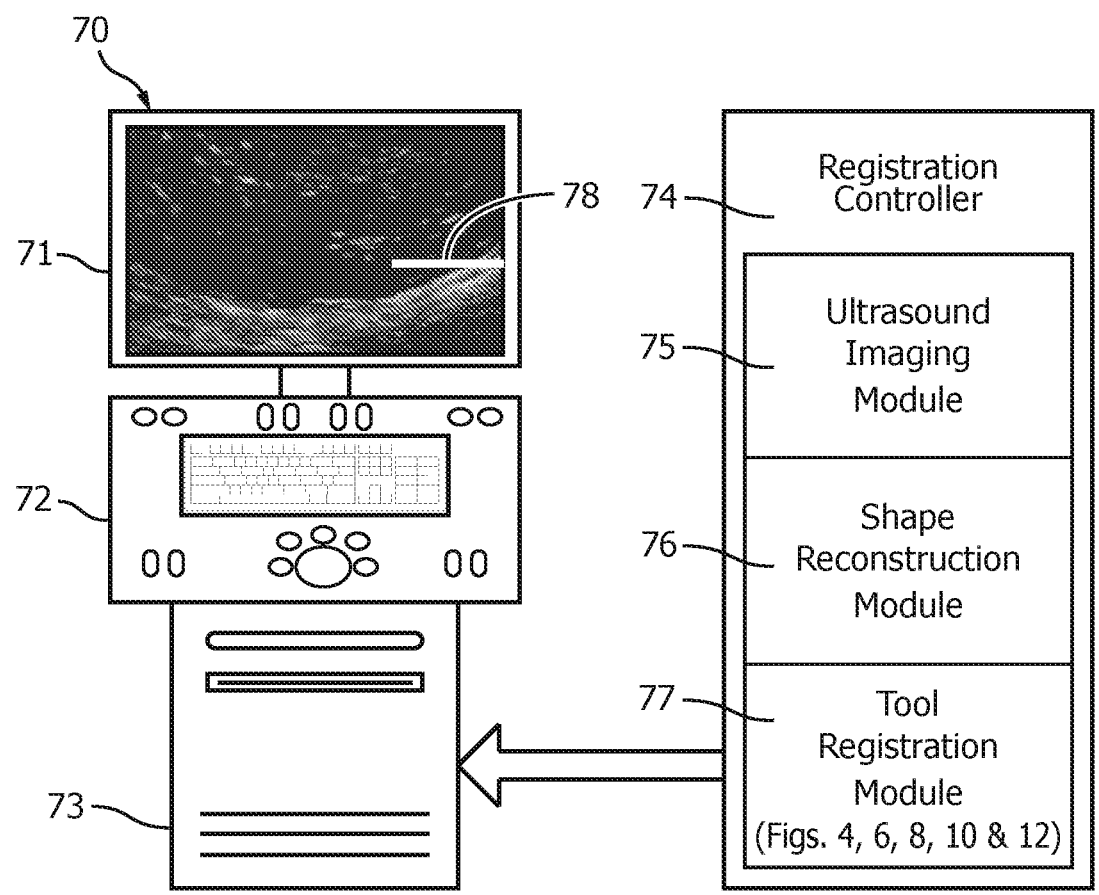

To facilitate an understanding of the present invention, exemplary embodiments of the present invention will be provided herein directed to a grid-based intervention system replacing a standard needle (e.g., needle 30 of FIG. 1) with an optical shape sensing ("OSS") needle (e.g., OSS needle 32 of FIG. 2) and providing a registration registration controller 74 for registering the OSS needle 32 to a grid (e.g., grid 50 of FIG. 2) and an ultrasound probe (e.g., TRUS probe 20 of FIG. 2). From description of the exemplary embodiments as shown in FIGS. 2-12, those having ordinary skill in the art will appreciate how to make and use the present invention for implementation within any grid-based interventional procedure (e.g., brachytherapy and biopsy procedures) involving one or more types of OSS tools (e.g., needle, catheters, guidewires) and one or more types of ultrasound probes (e.g., a TRUS probe).

For purposes of the present invention, the terms of the art including, but not limited to, "grid", "hub", "optical fiber", "seed applicator", "imaging", "reconstruction", "registration" and "coordinate system", are to be interpreted as known in the art of the present invention.

Referring to FIG. 2, OSS needle 32 is shown inserted within channel 51 of grid 50. In practice, optical sensors (not shown) may be embedded within/affixed onto OSS needle 32 in any arrangement suitable for reconstructing a segment/entire shape of OSS needle 32. In one embodiment, one or more optical fibers, each having fiber Bragg gratings, is(are) embedded within/affixed onto a brachytherapy/biopsy needle.

Also, for purposes of registration, a distal tip of OSS needle 32 may be disposed within channel 51 (not shown), or the distal tip of OSS needle 32 may be extended through channel 51 as shown in FIG. 2 whereby a distal segment 32D of OSS needle 32 may be inserted within an anatomical region (e.g., a prostate) and whereby either or both of distal segment 32D and proximal segment 32P of OSS needle 32 serve as the basis for estimating depth translational parameter $Z_{TP}$ and roll rotational parameter $Z_{RP}$.

Similarly to needle 30 (FIG. 1), hub 60 is attached to a proximal end of OSS needle 32 for establishing a needle coordinate system 33 having an origin at the proximal attachment point as shown in FIG. 2. Alternatively, an origin of a needle coordinate system may be established at any other point along an OSS needle of the present invention, such as, for example, the distal tip of OSS needle 32.

Optionally, a hub marker 61 may be attached to hub 60 to facilitate an insertion of OSS needle 32 into/through channel 51 at a known orientation for registration purposes as will be subsequently explained herein.

A registration machine 70 employs a monitor 71, an interface platform 72 and a workstation 73 as known in the art.

While not shown for clarity, those having ordinary skill in the art will appreciate how to couple TRUS probe 20 and OSS needle 32 to workstation 73 for purposes of processing ultrasound data and optical data, respectively.

Workstation 73 has a registration controller 74 installed therein.

Registration controller 74 includes and/or is accessible by an operating system (not shown) as known in the art for controlling various graphical user interfaces, data and images on monitor 71 as directed by a workstation operator (e.g., a doctor, technician, etc.) via a keyboard, buttons, dials, joysticks, etc. of interface platform 72, and for storing/reading data as programmed and/or directed by the workstation operator of interface platform 72.

For registration purposes, registration controller 74 further executes application modules including an ultrasound imaging module 75, a shape reconstruction module 76 and a tool registration module 77.

Ultrasound imaging module 75 is structurally configured within registration controller 74 to generate an ultrasound image relative to image coordinate system 21 from the ultrasound data provided by TRUS probe 20 as known in the art. In practice, the ultrasound data/image may have any form suitable for registration purposes. In one embodiment, the ultrasound image is a 3D ultrasound volume generated by a reconstruction of two-dimensional ("2D") parallel slices or by use of a 3D probe.

Shape reconstruction module 76 is structurally configured within registration controller 74 to reconstruct a segment/entire shape of OSS needle 32 relative to needle coordinate system 33 from the optical data provided by OSS needle 32 as known in the art.

Tool registration module 77 is structurally configured within registration controller 74 to register needle coordinate system 33 to pre-operatively/intra-operatively registered probe coordinate system 21 and grid coordinate system 52 in accordance with the present invention as subsequently described herein. In practice, registration controller 74 may include additional module(s) for pre-operatively/intra-operatively registering probe coordinate system 21 and grid coordinate system 52 as known in the art.

In operation, registration controller 74 controls the registration process as prompted by an operator of registration machine 70 in accordance with a particular embodiment of tool registration module 77. To this end, FIG. 3 illustrates a flowchart 130 representative of an intervention method of the present invention as controlled by registration controller 74 generally for any embodiment of tool registration module 77.

Figure 3:
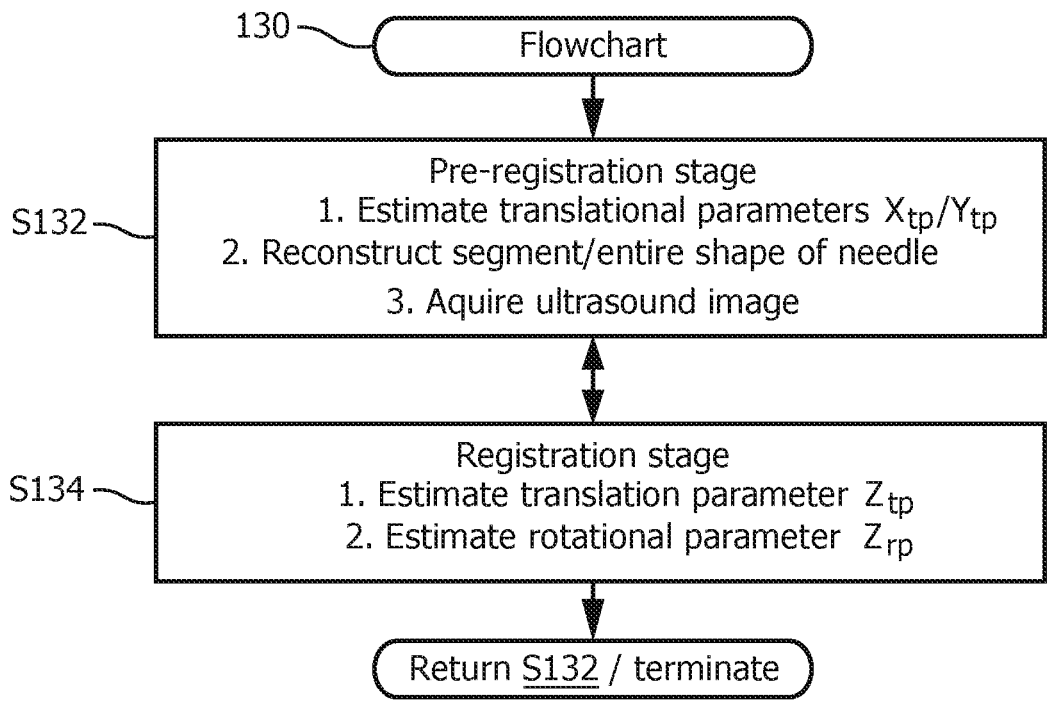
FIG. 3 illustrates a flowchart representative of an exemplary embodiment of an interventional method in accordance with the present invention.

Referring to FIG. 3, a pre-registration stage S132 of flowchart 130 encompasses an estimation of width translational parameter $X_{TP}$ and height translational parameter $Y_{TP}$. In practice, this estimation may be calculated by any manner suitable for registration purposes. In one embodiment, width translational parameter $X_{TP}$ and height translational parameter $Y_{TP}$ may be manually estimated based on a known position of a selected channel 51 within grid coordinate within 52. In a second embodiment, width translational parameter $X_{TP}$ and height translational parameter $Y_{TP}$ may be automatically estimated based on a use of a sensor (not shown) in or near grid 50 that detects a passage of OSS needle 32 into/through a specific channel 51. Alternatively, width translational parameter $X_{TP}$ and height translational parameter $Y_{TP}$ may be estimated during a registration phase 134 of flowchart 130 as will be subsequently described herein.

In practice, more than one OSS needle 32 may be registered sequentially or simultaneously by tool registration module 77. As such, pre-registration stage S132 of flowchart 130 further encompasses a reconstruction of a segment/entire shape of one or more OSS needles 32.

Pre-registration stage S132 of flowchart 130 optionally encompasses an acquisition of one or more ultrasound images depending on the embodiment of tool registration module 77. In practice, each ultrasound image may be associated with the reconstruction of a segment/entire shape of one or more OSS needle 32.

Upon completion or during stage S132, registration phase S134 of flowchart 130 encompasses a direct or an indirect estimation by tool registration module 77 of depth translational parameter $Z_{TP}$ and/or a direct or an indirect estimation by tool registration module 77 of roll rotational parameter $Z_{RP}$ as needed. To facilitate an understanding of registration phase S134, various embodiments of tool registration module 77 will now be described herein as shown in FIGS. 4-12.

Figure 4:
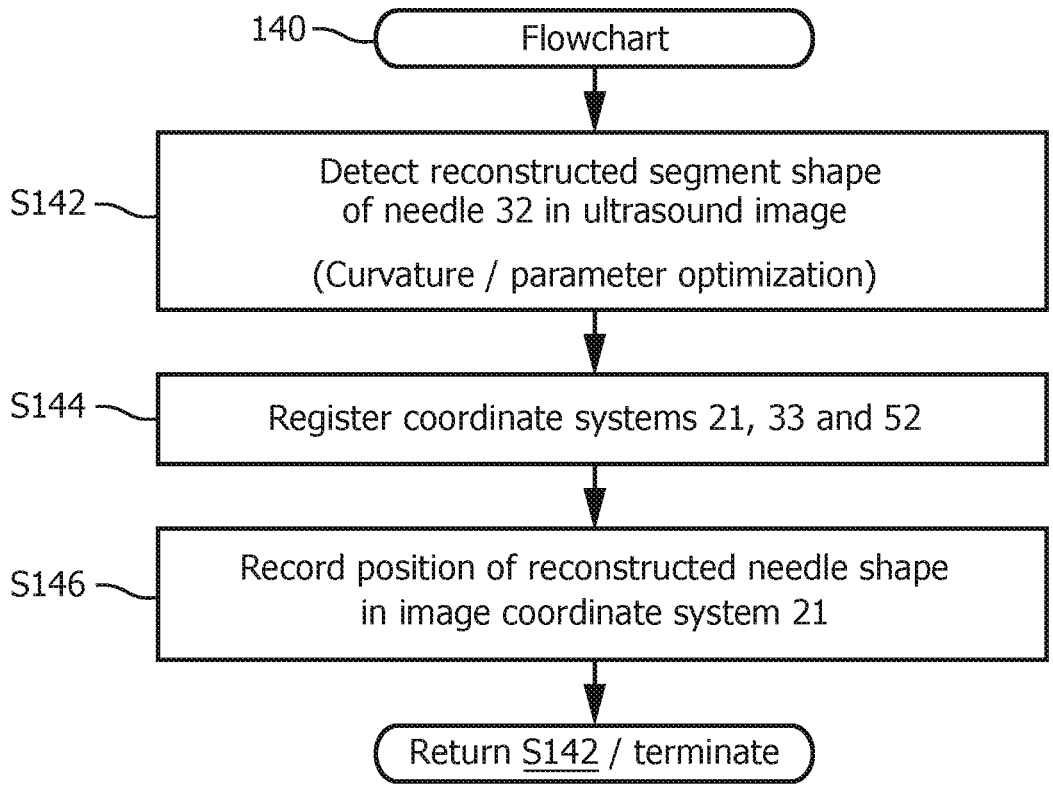
FIG. 4 illustrates a flowchart representative of a first exemplary embodiment of a needle registration method in accordance with the present invention.

Image-Based Registration. Referring to FIG. 4, a flowchart 140 is representative of an image-based needle registration method of the present invention for estimating depth translational parameter $Z_{TP}$ and roll rotational parameter $Z_{RP}$ of a OSS needle 32 from a detection of a reconstructed segment shape of one or more OSS needles 32 within the ultrasound image.

Specifically, for a single OSS needle 32, a pre-registration phase prior to flowchart 140 sequentially involves (1) an insertion of the distal tip of the OSS needle 32 into/through a channel 51 of grid 50 into the anatomical region, real or virtual, (2) a recording of a known position of channel 51 within grid coordinate system 52, (3) a reconstruction of an entire shape of OSS needle 32, and (4) an acquisition of ultrasound image of a segment of OSS needle 32 within the anatomical region.

Upon completion of the pre-registration phase, a stage S142 of flowchart 140 encompasses a detection by tool registration module 77 of the reconstructed segment of OSS needle 32 within the ultrasound image. A stage S144 of flowchart 140 encompasses registration by tool registration module 77 of coordinate systems 21, 33 and 52 as a function of the detected reconstructed segment of OSS needle 32 within the ultrasound image, and, a stage S146 of flowchart 140 encompasses a recording by tool registration module 77 of a position of the reconstructed shape of OSS needle 32 within image coordinate system 21 for purposes of displaying an icon of the reconstructed segment shape within the ultrasound image (e.g., icon 78 as shown in FIG. 2).

An exemplary implementation of flowchart 140 involves tool registration module 77 executing known technique(s) for identifying and segmenting needle-like structures in the ultrasound image. To this end, the known position of channel 51 within grid coordinate system 52 may be used to limit the processed region of the ultrasound image. In one embodiment, a matching curvature or shape of an identified needle segment(s) and the reconstructed entire shape of OSS needle 32 may be used to detect the reconstructed segment shape in the ultrasound image. In a second embodiment, the registration parameters may be optimized to maximize an overlap between the identified segmented structure(s) and the reconstructed segment shape in the ultrasound image. Also, the two embodiments may be combined.

Pre-registration stage and flowchart 140 are repeated for each OSS needle 32. Upon termination of flowchart 140, a tracking of the segment of OSS needle 32 with the ultrasound image facilitates the execution of the applicable interventional procedure including, but not limited to, permanent LDR seed implantation, HDR brachytherapy (temporary radioactive source insertion), transperineal biopsy, ablation, and cryotherapy. For example, with permanent LDR seed implantation, each seed position within the anatomical region may be planned from the recorded shape positions of the OSS needle(s) 32 within the ultrasound coordinate system 21.

Figure 5:
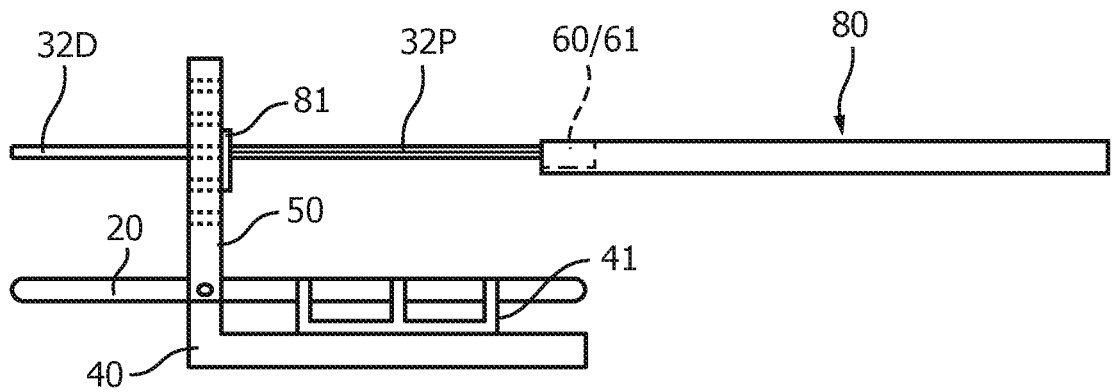
FIG. 5 illustrates an exemplary embodiment of brachytherapy set-up of an ultrasound probe, an optical shape sensing needle, a seed applicator, a steeper and a grid in accordance with the present invention.

Seed Applicator Registration. Referring to FIG. 5, this registration incorporates a seed applicator 80 to deliver seeds (not shown) to the anatomical region (not shown) as known in the art (e.g., a Mick® Applicator to deliver brachytherapy seeds to a prostate). Generally, as applied to OSS needles 32 of the present invention similarly to the art, each OSS needle is inserted through a channel 51 of grid 50 under ultrasound-guidance whereby a distal segment 32D extends into the anatomical region. To facilitate delivery of the seed, seed applicator 80 is subsequently attached to hub 60 and a guide ring 81 is extended over a proximal segment 32P of OSS needle 32 to grid 50. For this registration embodiment, an origin of the needle coordinate system being established at the distal tip of needle 32 preferably coincides the origin with each seed drop position.

Figure 6:
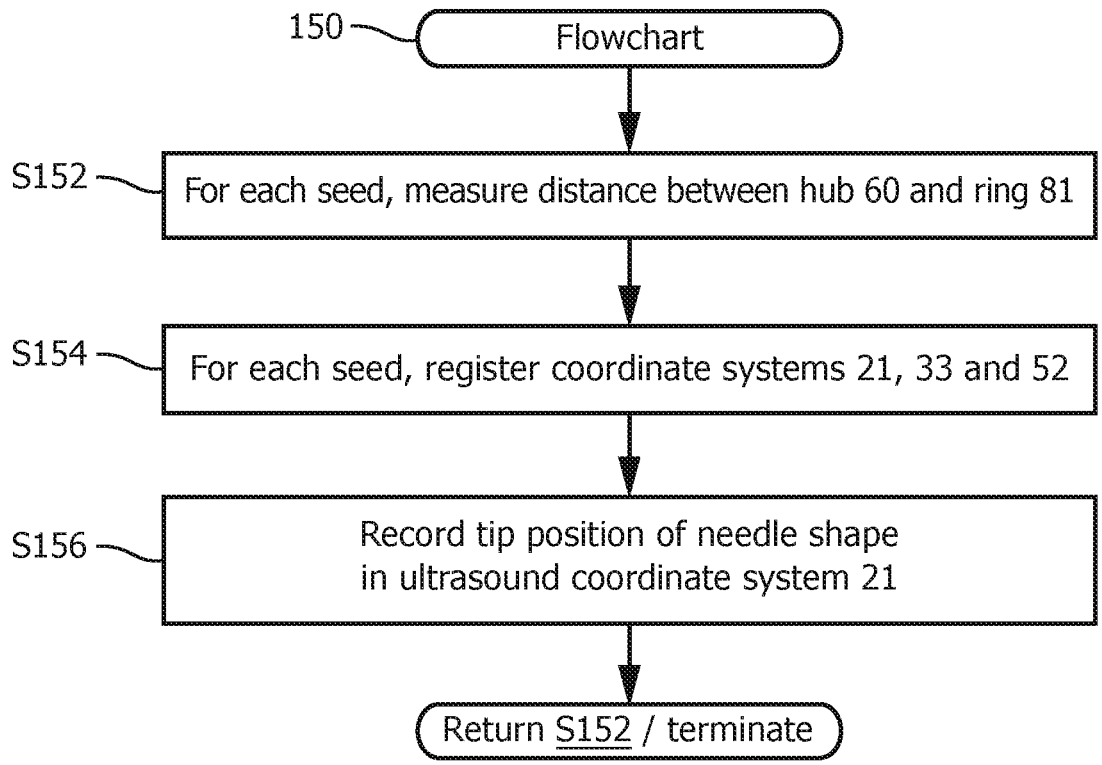
FIG. 6 illustrates a flowchart representative of a second exemplary embodiment of a needle registration method in accordance with the present invention.

Referring to FIG. 6, a flowchart 150 is representative of a seed applicator-based needle registration method of the present invention for estimating depth translational parameter $Z_{TP}$ from a measurement of a distance from hub 60 as attached by seed applicator 80 to grid ring 81 as adjacent grid 50, and for estimating rotational parameter $Z_{RP}$ of a OSS needle 32 from a positioning of hub 61 relative to seed applicator 80 (e.g., hub 60 is facing downward).

Specifically, for single OSS needle 32, a pre-registration phase prior to flowchart 150 sequentially involves (1) an insertion of the distal tip of the OSS needle 32 into/through a channel 51 of grid 50 whereby distal segment 32D extends into the anatomical region, real or virtual and (2) a recording of a known position of channel 51 within grid coordinate system 52. For each seed to be delivered by the single OSS needle 32, the pre-registration phase of flowchart 150 involve a reconstruction of a segment/entire shape of OSS needle 32.

Upon completion of the pre-registration phase, a stage S152 of flowchart 150 encompasses a measurement of a distance from hub 60 as attached by seed applicator 80 to guide ring 81 as adjacent grid 50. A stage S154 of flowchart 150 encompasses registration by tool registration module 77 of coordinate systems 21, 33 and 52 as a function of the measured distance from hub 60 as attached by seed applicator 80 to guide ring 81 as adjacent grid 50, and, a stage S156 of flowchart 150 encompasses a recording by tool registration module 77 of a position of the reconstructed shape of OSS needle 32 within image coordinate system 21 for purposes of displaying an icon of the reconstructed segment shape within the ultrasound image (e.g., icon 78 as shown in FIG. 2).

An exemplary implementation of flowchart 150 involves seed applicator 80 being to be used to (1) load brachytherapy seeds into an OSS needle 32 one-by-one, (2) push a seed out of OSS needle 32 and (3) retract OSS needle 32 by a predefined distance. As the seeds are dropped in the anatomical region, each location of seed drop is recorded by tool registration module 77 and used to update the treatment plan. More particularly, first, the OSS needle 32 is inserted to the desired depth with hub marker 61 looking downward. Seed applicator 80 grabs hub 60 and grid ring 81 is advanced to grid 50. At this point, the grid hole position, the hub marker orientation (looking down) and the distance from the hub 60 to grid 50 may be processed to register OSS needle 32 to grid 50 and hence, to the ultrasound volume. An obturator (not shown) of seed applicator 80 is retracted to load a seed into OSS needle 32. Then the obturator is pushed to drop the seed into the anatomical region. As the obturator reaches the end of its way, the hub distance to grid 50 may be used to localize the needle tip and seed drop position. This distance is measured manually or automatically by equipping seed applicator 80 with a sensor. This process is repeated until all the seeds are deposited. Therefore, the positions of all the seeds in an OSS needle 32 are estimated and is used for plan update as needed.

Figure 7:
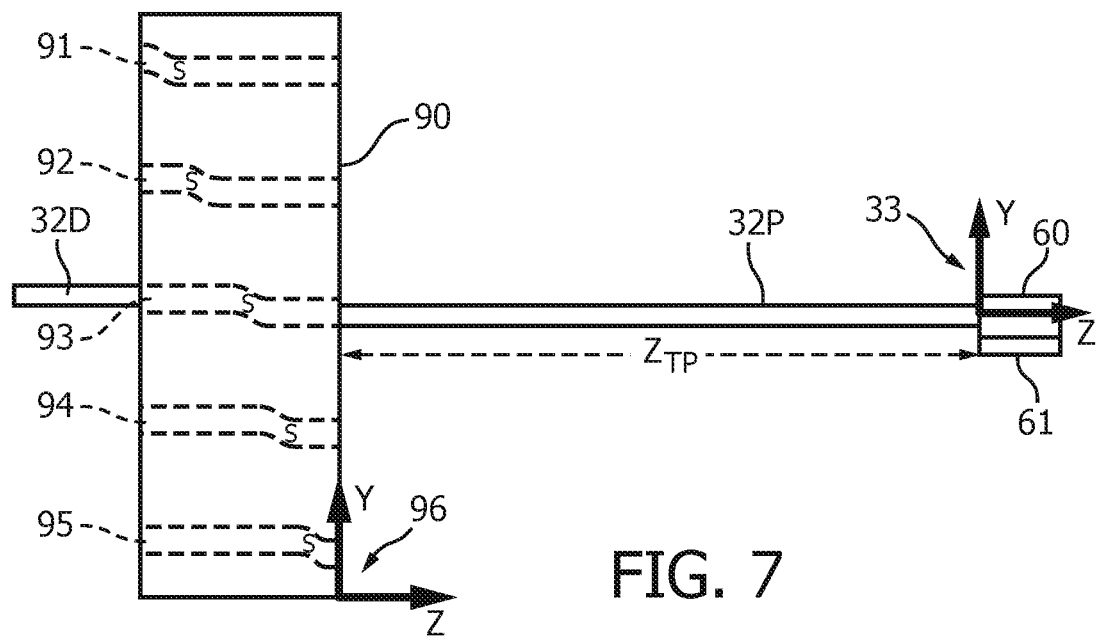
FIG. 7 illustrates an exemplary embodiment of brachytherapy set-up of an ultrasound probe, an optical shape sensing needle, a steeper and an irregular grid in accordance with the present invention.

Irregular Grid Registration. Referring to FIG. 7, this registration incorporates an irregular grid 90 as opposed to a regular grid 50 (FIG. 1). More particularly, for purposes of the present invention, the term "irregular grid" broadly encompasses a grid having a degree of shape inhomogeneity among two (2) or more channels to thereby distinguish the channels for registration purposes as opposed to having substantially, if not completely, shape homogeneity among all channels that impedes distinguishing the channels for registration purposes. For example, irregular grid 90 has shape inhomogeneity among channels 91-95 as shown to thereby distinguish channels 91-95 for registration purposes. In this example, a common upward point S-curve of channels is 91-95 is offset in a proximal direction for descending rows.

In practice, the shape of one or more grid channels may be unique for facilitating a determination of those grid channel(s) within the grid coordinate system based on the unique shape(s) as subsequently described herein.

Also in practice, an irregular grid of the present invention may be manufactured in accordance with standard manufacturing practice or may be manufactured as an attachment onto a standard grid that extends one or more of the grid channels into unique shape(s) (e.g., an attachment to a front side or a back side of grid 50 shown in FIG. 1).

Figure 8:
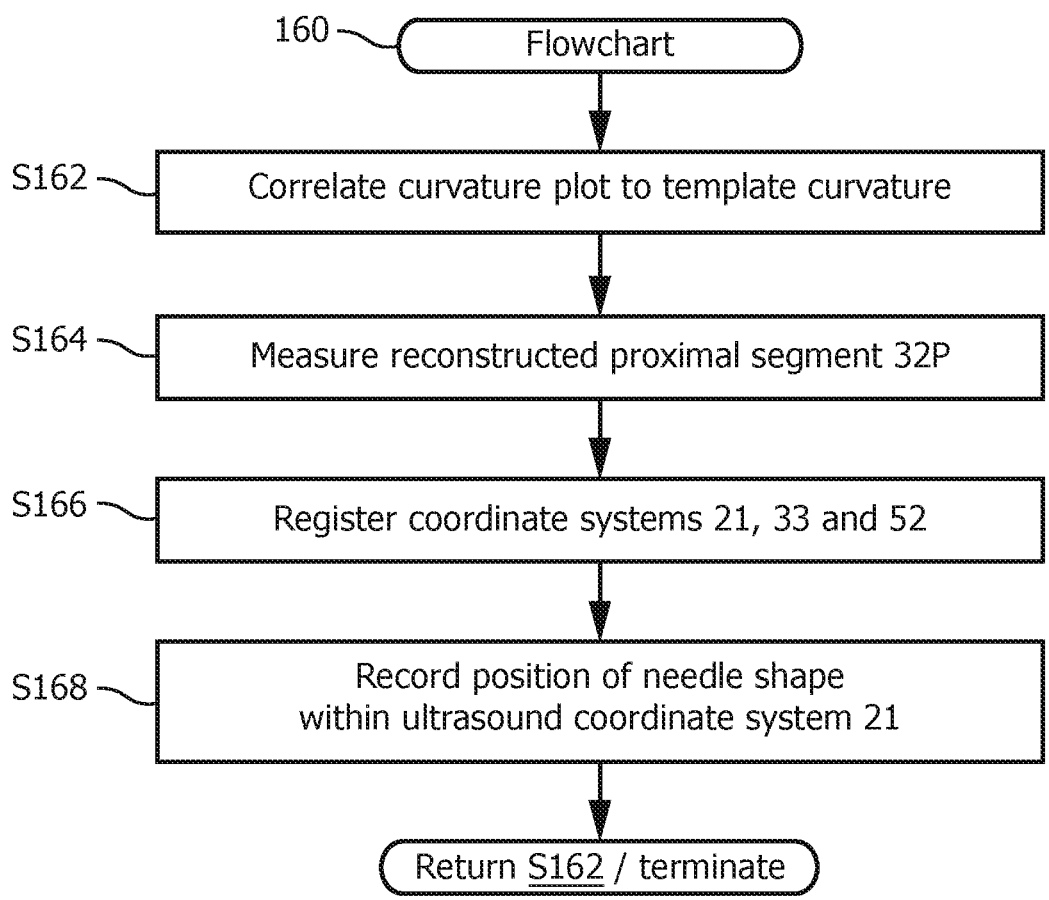
FIG. 8 illustrates a flowchart representative of a third exemplary embodiment of a needle registration method in accordance with the present invention.

Referring to FIG. 8, a flowchart 160 is representative of an irregular grid-based needle registration method of the present invention for estimating depth translational parameter $Z_{TP}$ and rotational parameter $Z_{RP}$ of a OSS needle 32 from a distinct shape of each channel of irregular grid 90, of which only channels 91-95 are shown.

Specifically, for single OSS needle 32, a pre-registration phase prior to flowchart 160 sequentially involves (1) an insertion of the distal tip of OSS needle 32 into/through a channel of irregular grid 90, and (2) a reconstruction of a segment/entire shape of OSS needle 32.

Upon completion of the pre-registration phase, a stage S162 of flowchart 160 encompasses a correlation by tool registration module 77 of a curvature plot of the reconstructed shape of OSS needle 32 to a template curvature of each channel of irregular grid 90 for identification of the appropriate channel. A stage S164 of flowchart 160 encompasses a measurement of a proximal segment 32P of OSS needle 32 relative to the template curvature of the identified channel. A stage S166 of flowchart 160 encompasses registration by tool registration module 77 of coordinate systems 21, 33 and 52 as a function of the measured proximal segment 32P of OSS needle 32 relative to the template curvature of the identified channel; and, a stage S168 of flowchart 160 encompasses a recording by tool registration module 77 of a position of the reconstructed shape of OSS needle 32 within image coordinate system 21 for purposes of displaying an icon of the reconstructed segment shape within the ultrasound image (e.g., icon 78 as shown in FIG. 2).

An exemplary implementation of flowchart 160 involves each shape of a channel of irregular grid 90 having only a gradual curvature that will permit the passage of OSS needle 32. Each channel shape may be unique whereby a channel is identified by analyzing the curvature of each channel shape whereby all translational parameters may be determined. Optionally, channel shapes may be repeated and the user identifies which grid hole is being used whereby translational parameters $X_{TP}$ and $Y_{TP}$ are known. A location of the inhomogeneity in the identified channel shape provides the estimation of depth translational parameters $Z_{TP}$. The curvature of the channel shape also provides the estimation of roll rotational parameters $Z_{RP}$. The origin of the optical shape sensing system is in the hub (or handle) of the needle. Thus, the needle can be registered to grid 90 and therefore, to the ultrasound image. More particular to curvature correlation, a unique curvature is visualized preferably at three (3) different points along the reconstructed shape of OSS needle 32. This curvature is uniquely identified using pattern matching with a template curvature for identifying a portion of the OSS needle 32 disposed within the template shape of a particular channel.

Figure 9A:
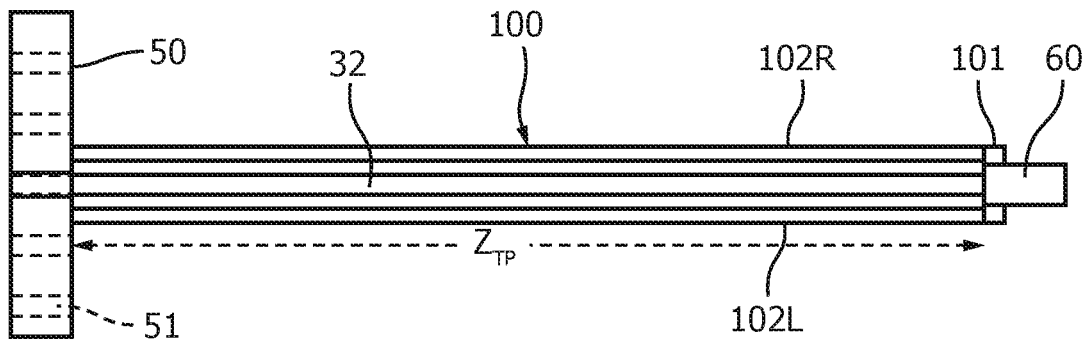
FIGS. 9A and 9B illustrate side view and a front view, respectively, of an exemplary embodiment of brachytherapy set-up of an ultrasound probe, an optical shape sensing needle, a needle bracket, a steeper and a grid in accordance with the present invention.
Figure 9B:
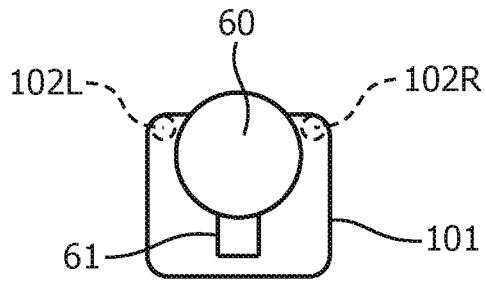

Needle Bracket Registration. Referring to FIGS. 9 A and B, this registration incorporates a needle bracket 100 to support an insertion of an OSS needle 32 into one of the channels 51 of grid 50. Generally, needle bracket 100 has a base 101 partially encircling hub 60 and hub marker 61, and a pair of rails 102R and 102L mounting needle bracket 100 to grid 50 adjacent a selected channel 51 of grid 50.

Figure 10:
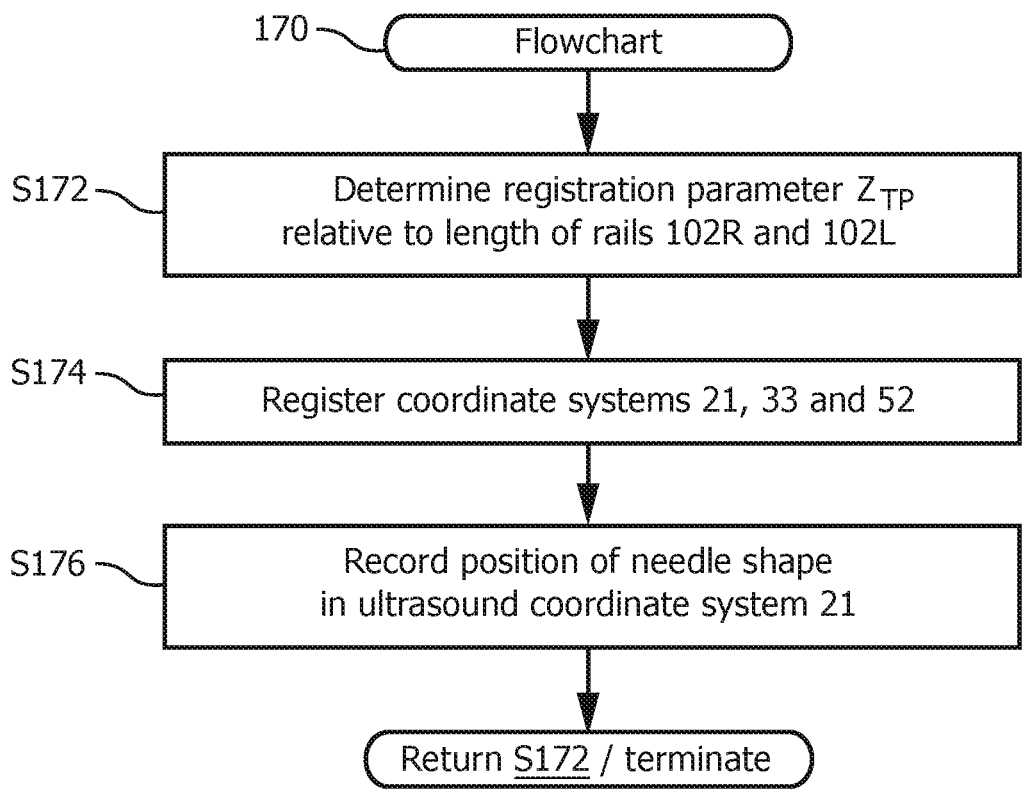
FIG. 10 illustrates a flowchart representative of a fourth exemplary embodiment of a needle registration method in accordance with the present invention.

Referring to FIG. 10, a flowchart 170 is representative of a needle bracket-based needle registration method of the present invention for estimating depth translational parameter $Z_{TP}$ from a length of rails 102R and 102L, and for estimating rotational parameter $Z_{RP}$ of a OSS needle 32 from a notch of base 101 partially encircling of hub 60 and hub marker 61 by base 101.

Specifically, for a single OSS needle 32, a pre-registration phase prior to flowchart 150 sequentially involves (1) an insertion of the distal tip of the OSS needle 32 into/through a channel 51 of grid 50 as supported by needle bracket 100, (2) a recording of a known position of channel 51 within grid coordinate system 52, and (3) a reconstruction of a segment/entire shape of OSS needle 32.

Upon completion of the pre-registration phase, a stage S172 of flowchart 170 encompasses tool registration module 77 determining depth translational parameter $Z_{TP}$ relative to a length of rails 102R and 102L. In one embodiment of stage S172, depth translational parameter $Z_{TP}$ equals to a length of rails 102R and 102L if the distal tip of OSS needle 32 is flush with grid 50. In second embodiment of stage S172, of the distance of OSS needle 32 along rails 102R and 102L may be measured, particularly when the distal tip of OSS needle 32 is spaced from the grid.

A stage S174 of flowchart 170 encompasses registration by tool registration module 77 of coordinate systems 21, 33 and 52 as a function of depth translational parameter $Z_{TP}$ equaling the length of rails 102R and 102L. A stage S176 of flowchart 170 encompasses a recording by tool registration module 77 of a position of the reconstructed shape of OSS needle 32 within image coordinate system 21 for purposes of displaying an icon of the reconstructed segment shape within the ultrasound image (e.g., icon 78 as shown in FIG. 2).

An exemplary implementation of flowchart 170 involves a retrofit of needle bracket 100 to existing commercial grids, such as, for example, grid 50. An attachment of needle bracket 100 to grid 50 may use a magnetic notch to attach to grid 50 or any other suitable attachment means. As shown, hub 60 and hub marker 61 fit snugly in needle bracket 100 thereby fixing roll rotational parameter $Z_{RP}$ relative to grid 50. Further, since base 101 of needle bracket 100 is at a known depth from grid 50, OSS needle 32 is registered to grid 50 and therefore the ultrasound image when OSS needle 32 is located in notch of base 101. In one embodiment, a depth of insertion of OSS needle 32 into the anatomical region is determined by a change in temperature as OSS needle 32 enters the anatomical region. Known curvature signatures may enhance this embodiment as known in the art. Optionally, needle bracket 100 is fitted with a relative position encoder (not shown) that estimates a magnitude of needle motion along needle bracket 100 (i.e., perpendicular to the grid) relative to the registration point (notch) on base 101.

Figure 11:
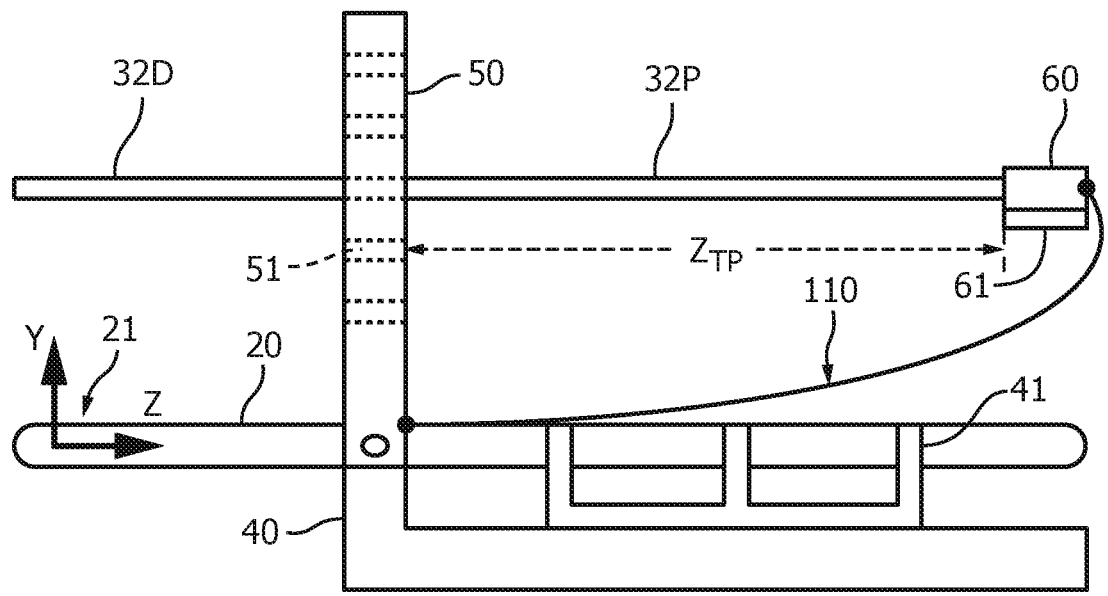
FIG. 11 illustrates an exemplary embodiment of brachytherapy set-up of an ultrasound probe, an optical shape sensing needle, an optical fiber, a steeper and a grid in accordance with the present invention.
Figure 12:
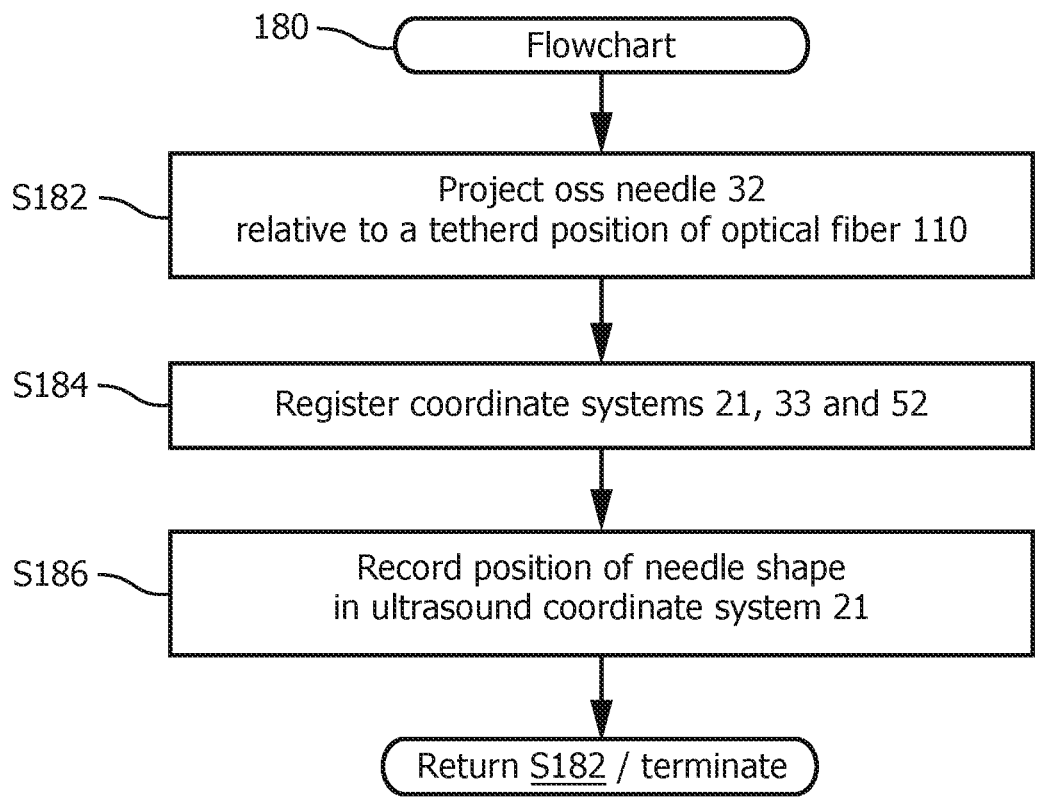
FIG. 12 illustrates a flowchart representative of a fifth exemplary embodiment of a needle registration method in accordance with the present invention.

Optical Fiber Registration. Referring to FIG. 11, this registration incorporates an optical fiber 110 to project OSS needle 32 relative to a tethered position of optical fiber 110 to grid 50. Generally, optical fiber 110 is connected to grid 50 (e.g., lower left corner of grid 50 as shown) and hub 60 (e.g., an open face as shown). More particularly, optical fiber 110 may be connected in a manner that registers the optical fiber 110 to the grid coordinate system and optionally to the needle coordinate system. (e.g., connection at or adjacent to the origin of grid coordinate system and the needle coordinate system). A reconstructed shape of optical fiber 110 facilitates a projection of a reconstructed shape of OSS needle 32 relative to the tethered position of optical fiber 110 to grid 40, which facilitates a registration of OSS needle 32 to image coordinate system 21.

Specifically, for a single OSS needle 32, a pre-registration phase prior to flowchart 180 (referring to FIG. 12) involves (1) an insertion of the distal tip of the OSS needle 32 (shown in FIG. 12 as distal segment 32D and proximal segment 32P) into/through a channel 51 of grid 50 and (2) a reconstruction of an entire shape of OSS needle 32.

Upon completion of the pre-registration phase, a stage S182 of flowchart 180 encompasses tool registration module 77 reconstructing an entire shape of optical fiber 110 to thereby project the reconstructed shape of OSS needle 32 relative to the tethered position of optical fiber 110 to grid 50 through the selected channel of grid 50. A stage S184 of flowchart 180 encompasses registration by tool registration module 77 of coordinate systems 21, 33 and 52 as a function of the projected reconstructed shape of OSS needle 32. A stage S186 of flowchart 180 encompasses a recording by tool registration module 77 of a position of the reconstructed shape of OSS needle 32 within image coordinate system 21 for purposes of displaying an icon of the reconstructed segment shape within the ultrasound image (e.g., icon 78 as shown in FIG. 2).

Optionally, probe 20 may be equipped with an optical fiber(s) and similarly registered to grid 50 based on a reconstruction of the shape of the optical fiber(s). The registration may be performed at a known position of probe 20 with respect to grid 50.

Post-Registration. Referring back to FIG. 3, upon completion of flowchart 130 by the particular embodiment of tool registration module 77, the registered OSS needle 33 is tracked by tool registration module 77 or an additional tracking module of registration controller 74. In practice, the tracking of the registered OSS needle 33 may be implemented by various tracking methods known in the art. In one embodiment as previously described herein with the needle bracket registration, depth of insertion of OSS needle 32 into the anatomical region is determined by a change in temperature along OSS needle 32 as OSS needle 32 enters into/is navigated within the anatomical region. More particularly, referring to FIG. 2, a placement of grid abutting the anatomical region facilitates a registration of needle coordinate system 21 to the grid coordinate system 52 based on a detection of any temperature change along a reconstruction of OSS needle 32 as OSS needle 32 is inserted into the anatomical region.

Also in practice, OSS needle 32 may be re-registered as needed or desired during the interventional procedure.

Referring to FIGS. 2-12, from the description of the exemplary embodiments of the present invention, those having ordinary skill in the art will appreciate numerous benefits of an intervention system and method of the present invention including, but not limited to, registered real-time 3D tracking and imaging for any grid-based interventional procedure.

Furthermore, as one having ordinary skill in the art will appreciate in view of the teachings provided herein, features, elements, components, etc. described in the present disclosure/specification and/or depicted in the FIGS. 1-12 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 1-12 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for registration of an OSS tool, (which embodiments are intended to be illustrative and not limiting), it is noted that modifications and variations can be made by persons having ordinary skill in the art in light of the teachings provided herein, including the FIGS. 1-12. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. An intervention system comprising:
an optical shape sensing tool configured to generate shape data indicative of a shape of the optical shape sensing tool;
a grid operable to guide an insertion of a distal end of optical shape sensing tool into an anatomical region relative to a grid coordinate system;
an ultrasound probe registered to the grid coordinate system and configured to generate image data of the anatomical region; and
one or more processors configured to:
reconstruct a shape of at least a segment of the distal end of the optical shape sensing tool in a needle coordinate system having an origin at a point on the optical shape sensing tool from the shape data generated by the optical shape sensing tool,
generate an ultrasound image of the anatomical region including at least the segment of the distal end of the optical shape sensing tool in an image coordinate system registered to the grid coordinate system from the image data,
detect the shape of at least the segment of the distal end of the optical shape sensing tool within the ultrasound image, and
register the needle coordinate system to at least one of the grid and image coordinate systems based on the reconstructed shape of at least the segment of the distal end of the optical shape sensing tool and the detected shape of the distal end within the ultrasound image.

2. The intervention system of claim 1, wherein the one or more processors is further configured to generate an icon of the reconstructed shape of the at least the segment of the distal end of the optical shape sensing tool for display overlaid on the ultrasound image.

3. The intervention system of claim 1, further comprising:
an optical fiber connected to the ultrasound probe and in communication with the one or more processors; and
wherein the one or more processors are further configured to register the image coordinate system to the grid coordinate system based on a reconstructed shape of the optical fiber indicating a tethering location on the grid relative to an origin of the image coordinate system.

4. The intervention system of claim 1, further comprising:
a seed applicator attached to the optical shape sensing tool to measure a distance between the grid and the origin of the needle coordinate system; and
wherein the one or more processors are further configured to register the needle coordinate system to the grid coordinate system based on a measurement by the seed applicator of the distance between the grid and the origin of the needle coordinate system.

5. The intervention system of claim 1, further comprising:
a needle bracket supporting the optical shape sensing tool configured to measure a distance between the grid and the origin of the needle coordinate system; and
wherein the one or more processors are further structurally configured to use the needle bracket to determine a distance between the grid and the origin of the needle coordinate system.

6. The intervention system of claim 1, wherein the one or more processors are further structurally configured to:
detect a temperature change along the optical shape sensing tool,
based on the detected temperature change, determine depth of insertion of the optical shape sensing tool into the anatomical region.

7. The intervention system of claim 1, wherein the one or more processors are further configured to register the needle coordinate system to the grid coordinate system as a function of a measurement a distance between the grid and the origin of the needle coordinate system.

8. An intervention system comprising:
an optical shape sensing tool configured to generate shape data indicative of a shape of at least a segment of the optical shape sensing tool; a grid having a plurality of channels operable to guide an insertion of the optical shape sensing tool into an anatomical region relative to a grid coordinate system, at least one of the channels being of inhomogeneous shape including a curve such that during insertion of the optical shape sensing tool through one of the channels, the optical shape sensing tool is bent by the curvature of the channel; and
one or more processors in communication with the optical shape sensing tool configured to:
reconstruct a shape of at least the segment of the optical shape sensing tool relative to a needle coordinate system having an origin at a point on the optical shape sensing tool from the shape data, and, register the needle coordinate system to the grid coordinate system based on a correlation of the curvature of a reconstructed segment of the optical shape sensing tool to a template curvature for each irregular channel of the grid having the inhomogeneous shape.

9. The intervention system of claim 8, wherein each of the plurality of channels has different curvature characteristics and
the one or more processors are further configured to determine through which of the plurality of channels the optical shape sensing tool is inserted into the anatomical region based on the reconstructed segment of the optical shape sensing tool.

10. The system of claim 8 wherein the channels have S-shaped curvatures.

11. An intervention system comprising:
an optical shape sensing tool;
a grid operable to guide an insertion of the optical shape sensing tool into an anatomical region relative to a grid coordinate system;
an optical fiber connected to the optical shape sensing tool and tethered to the grid;
one or more processors configured to:
reconstruct a shape of at least a segment of the optical shape sensing tool relative to a needle coordinate system having an origin at a point on the optical shape sensing tool,
reconstruct a shape of the optical fiber indicating a tethering location on the grid, and
register the needle coordinate system to the grid coordinate system using the shape of the optical fiber.

12. The intervention system of claim 11, wherein the one or more processors are further configured to:
- detect temperature change along the optical shape sensing tool; and
- determine a depth of insertion into the anatomical region based on the detected temperature change along the optical shape sensing tool.

\* \* \* \* \*